(12) United States Patent
Stearns et al.

(10) Patent No.: US 11,224,512 B2
(45) Date of Patent: Jan. 18, 2022

(54) CORONARY ARTERY CHECK VALVE

(71) Applicant: Edwards Lifesciences Corporation, Irvine, CA (US)

(72) Inventors: Grant Matthew Stearns, Tustin, CA (US); Gregory Bak-Boychuk, San Clemente, CA (US); Sergio Delgado, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/293,306

(22) Filed: Mar. 5, 2019

(65) Prior Publication Data

US 2019/0290434 A1 Sep. 26, 2019

Related U.S. Application Data

(60) Provisional application No. 62/646,241, filed on Mar. 21, 2018.

(51) Int. Cl.
*A61F 2/24* (2006.01)
*A61F 2/86* (2013.01)
*A61F 2/848* (2013.01)

(52) U.S. Cl.
CPC .......... *A61F 2/2469* (2013.01); *A61F 2/2427* (2013.01); *A61F 2/86* (2013.01); *A61F 2/2418* (2013.01); *A61F 2/2436* (2013.01); *A61F 2002/8486* (2013.01); *A61F 2210/0014* (2013.01); *A61F 2230/0067* (2013.01); *A61F 2230/0091* (2013.01); *A61F 2250/0018* (2013.01); *A61F 2250/0048* (2013.01)

(58) Field of Classification Search
CPC ......... A61F 2/24; A61F 2/2427; A61F 2/2469
USPC ................................ 623/1.15–2.19
See application file for complete search history.

(56) References Cited

U.S. PATENT DOCUMENTS

| | | |
|---|---|---|
| 3,417,777 A | 12/1968 | De Balsac |
| 6,705,585 B1 | 3/2004 | Roy |
| 7,544,160 B2 | 6/2009 | Gross |
| 7,618,446 B2 * | 11/2009 | Andersen ............... A61F 2/2418 623/1.26 |
| 8,348,997 B2 * | 1/2013 | Thompson ............ A61F 2/2418 623/2.1 |
| 8,377,115 B2 | 2/2013 | Thompson |
| 9,017,351 B2 * | 4/2015 | Rudakov .......... A61B 17/12145 606/158 |

(Continued)

FOREIGN PATENT DOCUMENTS

| | | |
|---|---|---|
| DE | 3207690 A1 | 9/1983 |
| DE | 4204138 C2 | 9/1995 |

(Continued)

*Primary Examiner* — Suzette J Gherbi

(57) ABSTRACT

A coronary artery check valve includes a stent configured to attach to an inner wall of a coronary artery of a living subject, and a tapered helical coil coupled to the stent and configured to regulate blood flow in the coronary artery. The coronary artery check valve is configured to prevent retrograde flow of the coronary blood supply during diastole by closing during systole of the heart when the tapered helical coil compresses longitudinally, and opening when the tapered helical coil expands longitudinally to permit blood flow into the coronary artery when a coronary pressure of the living subject drops below diastolic blood pressure.

3 Claims, 9 Drawing Sheets

(56) References Cited

U.S. PATENT DOCUMENTS

| | | | |
|---|---|---|---|
| 10,765,519 B2* | 9/2020 | McGuckin, Jr. | A61F 2/2475 |
| 2006/0178552 A1* | 8/2006 | Gross | A61F 2/2421 |
| | | | 600/16 |
| 2007/0038293 A1* | 2/2007 | St.Goar | A61B 17/00234 |
| | | | 623/2.11 |
| 2010/0217385 A1* | 8/2010 | Thompson | A61F 2/2412 |
| | | | 623/2.36 |
| 2012/0290083 A1 | 11/2012 | Fargahi et al. | |
| 2014/0200654 A1* | 7/2014 | Shulze | A61L 31/06 |
| | | | 623/1.16 |
| 2014/0214153 A1* | 7/2014 | Ottma | A61F 2/2436 |
| | | | 623/2.11 |
| 2017/0245977 A1 | 8/2017 | Foster et al. | |
| 2019/0021860 A1* | 1/2019 | Keane | A61F 2/2454 |
| 2020/0205962 A1* | 7/2020 | Karavany | A61F 2/07 |

FOREIGN PATENT DOCUMENTS

| | | |
|---|---|---|
| FR | 1464202 A | 12/1966 |
| FR | 2407708 A1 | 6/1979 |
| WO | 2013037005 A1 | 3/2013 |

* cited by examiner

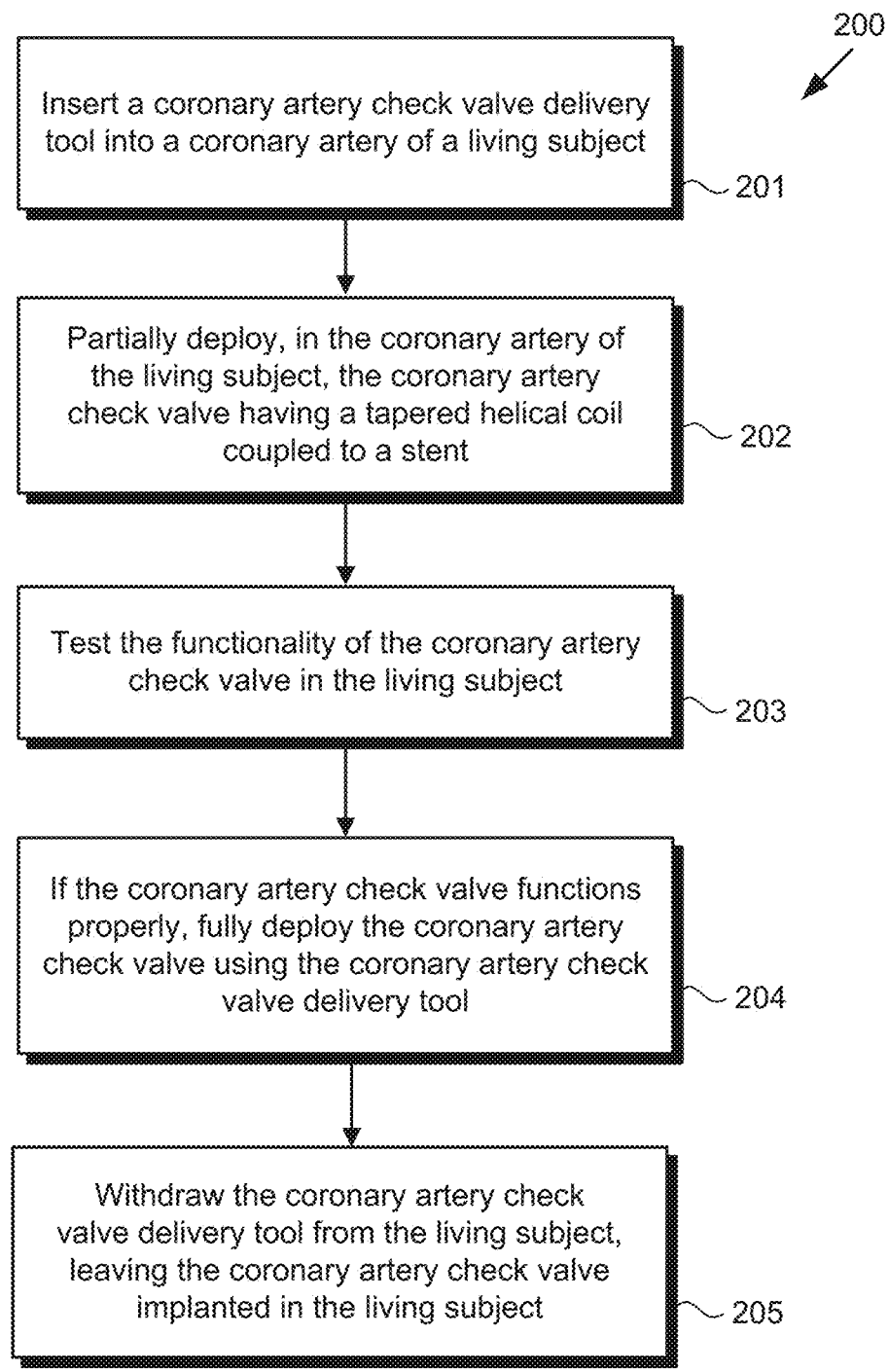

CORONARY ARTERY CHECK VALVE

RELATED APPLICATION(S)

The present application claims the benefit of and priority to Provisional Patent Application Ser. No. 62/646,241, filed Mar. 21, 2018, and titled "Coronary Artery Check Valve," which is hereby incorporated fully by reference into the present application.

BACKGROUND

Diastolic heart failure (DHF) is present when the left ventricle of the heart fails to adequately fill with blood during the diastole, or relaxation phase, of the cardiac cycle. The present standard of care for a patient diagnosed with DHF is treatment with beta blocker drugs, which slow the heart rate, thereby resulting in an increase in ventricular fill time. In addition, the administration of beta blockers is associated with a decrease in diastolic blood pressure, which can be beneficial. For example, when diastolic blood pressure is reduced to 60 mmHg, the left ventricular ejection fraction (LVEF) has been shown to increase by approximately 20%.

However, other, less salutary effects of reducing diastolic blood pressure can compromise the effectiveness of DHF treatment using beta blockers. For instance, reduction of diastolic blood pressure to below 85 mmHg has been shown to result in an approximately 26% decrease in coronary blood flow. Unfortunately, while increasing LVEF through the administration of beta blockers has a positive effect on patients suffering from DHF, the decrease in coronary blood flow associated with the reduction in diastolic blood pressure may weaken the already hypertrophic ventricle of such patients. Consequently, there is a need in the art for a treatment solution, suitable for use in combination with the administration of beta blockers, that maintains the desirable increase in LVEF associated with use of those drugs, while avoiding reduction in coronary blood flow.

SUMMARY

There are provided coronary artery check valves, as well as methods for their implantation in a living subject, substantially as shown in and/or described in connection with at least one of the figures, and as set forth more completely in the claims.

BRIEF DESCRIPTION OF THE DRAWINGS

FIG. 2 is a flowchart showing an exemplary method for implanting a coronary artery check valve in a living subject;

DETAILED DESCRIPTION

Figure 1A:
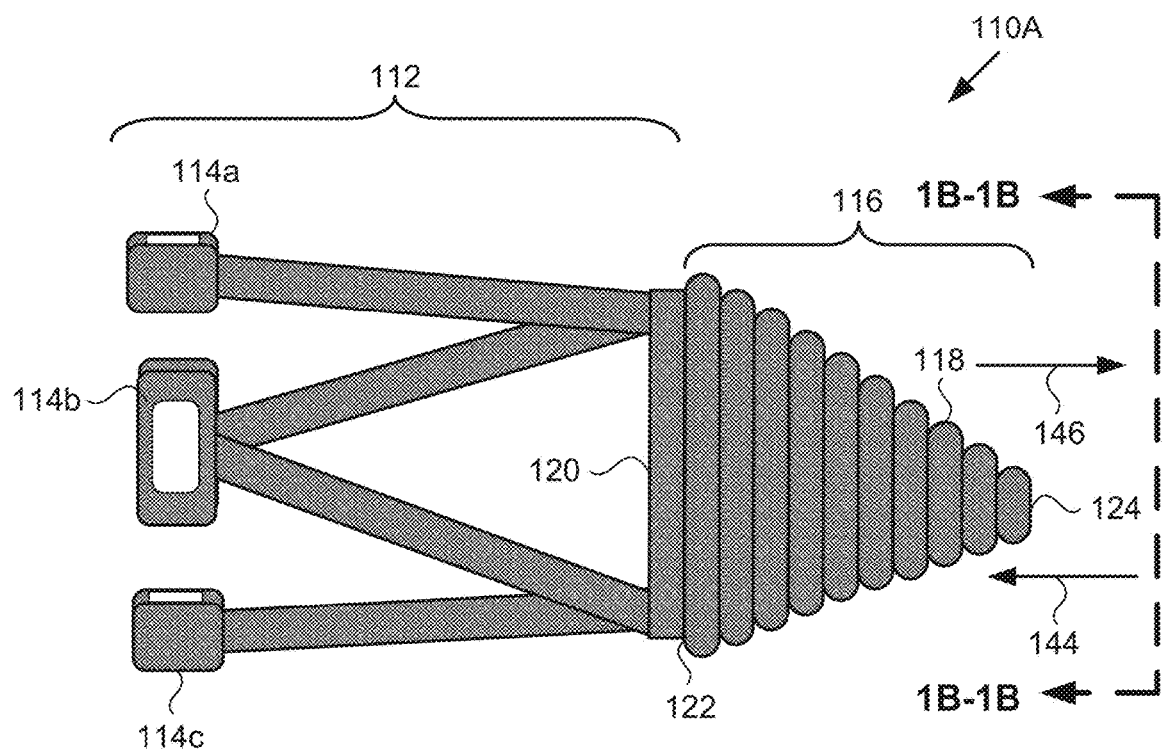
FIG. 1A shows a side view of an exemplary coronary artery check valve in a closed state, according to one implementation.

The following description contains specific information pertaining to implementations in the present disclosure. One skilled in the art will recognize that the present disclosure may be implemented in a manner different from that specifically discussed herein. The drawings in the present disclosure and their accompanying detailed description are directed to merely exemplary implementations. Unless noted otherwise, like or corresponding elements among the figures may be indicated by like or corresponding reference numerals. Moreover, the drawings and illustrations in the present disclosure are generally not to scale, and are not intended to correspond to actual relative dimensions.

The present application discloses a coronary artery check valve and method for its implantation that overcomes the drawbacks and deficiencies of the conventional art. The coronary artery check valve disclosed herein may be implanted in one or both of the coronary ostia, or at any point along the coronary arteries, to prevent retrograde flow of the coronary blood supply during diastole. The coronary artery check valve is configured to allow the coronary artery in which it is implanted to reach systolic blood pressure during systole, and to remain at systolic blood pressure until the coronary pressure drops below diastolic blood pressure. When the coronary pressure drops below diastolic blood pressure, the coronary artery check valve is further configured to open so as to advantageously allow additional blood flow into the coronary artery. In some implementations, implantation of the coronary artery check valve results is a coronary blood pressure in a range between systole and diastole of a patient on beta blockers, which may be close to 85 mmHg Consequently, the coronary artery check valve disclosed in the present application is suitable for use in combination with beta blockers, thereby enabling the desirable increase in LVEF associated with use of those drugs, while advantageously avoiding reduction in coronary blood flow due to low diastolic blood pressure.

FIG. 1A shows a side view of exemplary coronary artery check valve 110A in a closed state, according to one implementation. As shown in FIG. 1A, coronary artery check valve 110A includes stent 112 and tapered helical coil 116 formed from wire 118 and having proximal end 122 coupled to end 120 of stent 112. Also shown in FIG. 1A are anchors 114a, 114b, and 114c of stent 112, distal end 124 of tapered helical coil 116, and directions of respective compression and expansion 144 and 146 of tapered helical coil 116.

It is noted that although exemplary coronary artery check valve 110A is depicted in FIG. 1A as having tapered helical coil 116 formed from single wire 118, that representation is merely exemplary. In other implementations, as described below, tapered helical coil 116 may include two or more wires. Moreover, although tapered helical coil 116 is shown to have proximal end 122 coupled to end 120 of stent 112 so that distal end 124 of tapered helical coil 116 extends beyond stent 112 when exemplary coronary artery check valve 110A is closed, i.e., distal end is outside of stent 112 when coronary artery check valve 110A is closed, that representation is also merely exemplary. In other implementations, tapered helical coil 116 may be situated within stent 112 so as to be surrounded by stent 112.

Figure 1B:
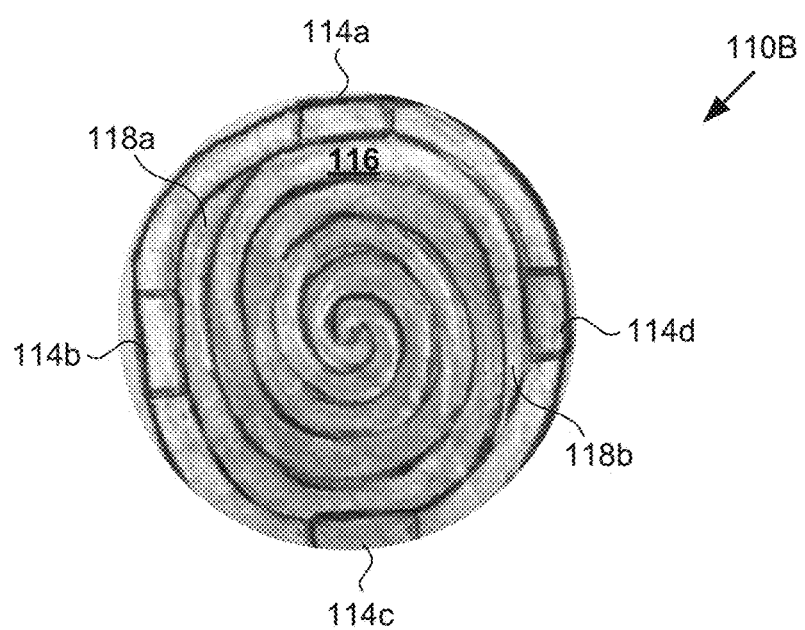
FIG. 1B shows an end view of an exemplary coronary artery check valve, according to one implementation, along perspective lines 1B-1B shown in FIG. 1A.

FIG. 1B shows an end view of exemplary coronary artery check valve 110B, according to one implementation, along perspective lines 1B-1B in FIG. 1A. Referring to FIG. 1B in combination with FIG. 1A, coronary artery check valve 110B includes stent 112 having anchors 114a, 114b, 114c, and 114d, as well as tapered helical coil 116 coupled to end 120 of stent 112. Coronary artery check valve 110B including stent 112 and tapered helical coil 116 corresponds in general to coronary artery check valve 110A, in FIG. 1A, and those corresponding features may share any of the characteristics attributed to either corresponding feature by the present disclosure.

One difference between coronary artery check valve 110A and coronary artery check valve 110B is that tapered helical coil 116 is implemented using single wire 118 in FIG. 1A, while tapered helical coil 116 is implemented using two interlaced wires 118a and 118b in FIG. 1B. It is emphasized that in various implementations, tapered helical coil 116 can be formed from a single wire, e.g., wire 118, or from two or more interlaced wires, e.g., wires 118a and 118b. Whether implemented as single wire 118 or as two or more interlaced wires 118a and 118b, wires 118/118a/118b may be formed of an alloy including nickel and titanium, such as nitinol.

It is noted that anchors 114a, 114b, 114c, and 114d, in FIG. 1B, are shown as though "seen through" wires 118a and 118b at proximal end 122 of tapered helical coil 116. It is further noted that anchor 114d, shown in FIG. 1B, may also be included in the implementation shown in FIG. 1A, but is not visible from the perspective shown by that figure.

As described in greater detail below, stent 112 is configured to attach to an inner wall of a coronary artery of a living subject using anchors 114a, 114b, 114c, and 114d. Tapered helical coil 116 is configured to regulate blood flow in the coronary artery of the living subject by selectively compressing longitudinally, i.e., in direction 144, and expanding longitudinally, i.e., in direction 146. Moreover, coronary artery check valve 110A/110B is configured to prevent retrograde flow of the coronary blood supply of the living subject during diastole of the heart of the living subject. Specifically, coronary artery check valve 110A/110B is configured to prevent retrograde flow of the coronary blood supply during diastole by closing during systole of the heart when tapered helical coil 116 compresses longitudinally in direction 144, and opening when tapered helical coil 116 expands longitudinally in direction 146 to permit blood flow into the coronary artery when a coronary pressure of the living subject drops below diastolic blood pressure.

The functionality of coronary artery check valve 110A/110B will be further described by reference to FIG. 2, as well as to FIGS. 3A, 3B, 3C, and 3D. FIG. 2 shows flowchart 200 of an exemplary method for implanting a coronary artery check valve in a living subject. Certain details and features have been left out of flowchart 200 that are apparent to a person of ordinary skill in the art. Actions 201 through 205 indicated in flowchart 200 are sufficient to describe one implementation of the present method; however, other implementations may utilize actions different from those shown in flowchart 200, and may include more, or fewer, actions. It is noted that the actions shown in flowchart 200 may be performed in a coronary ostia, or at any point along a coronary artery of a living subject.

Cross-sectional side views 300A, 300B, 300C, and 300D, shown respectively in FIGS. 3A through 3D, illustrate the result of performing the actions of flowchart 200. For example, cross-sectional side view 300A shows a portion of a coronary artery of a living subject subsequent to action 201, cross-sectional side view 300B shows a portion of the coronary artery of the living subject subsequent to actions 202 and 203, cross-sectional side view 300C shows a portion of the coronary artery of the living subject subsequent to action 204, and cross-sectional side view 300D shows a portion of the coronary artery of the living subject subsequent to action 205.

Figure 3A:
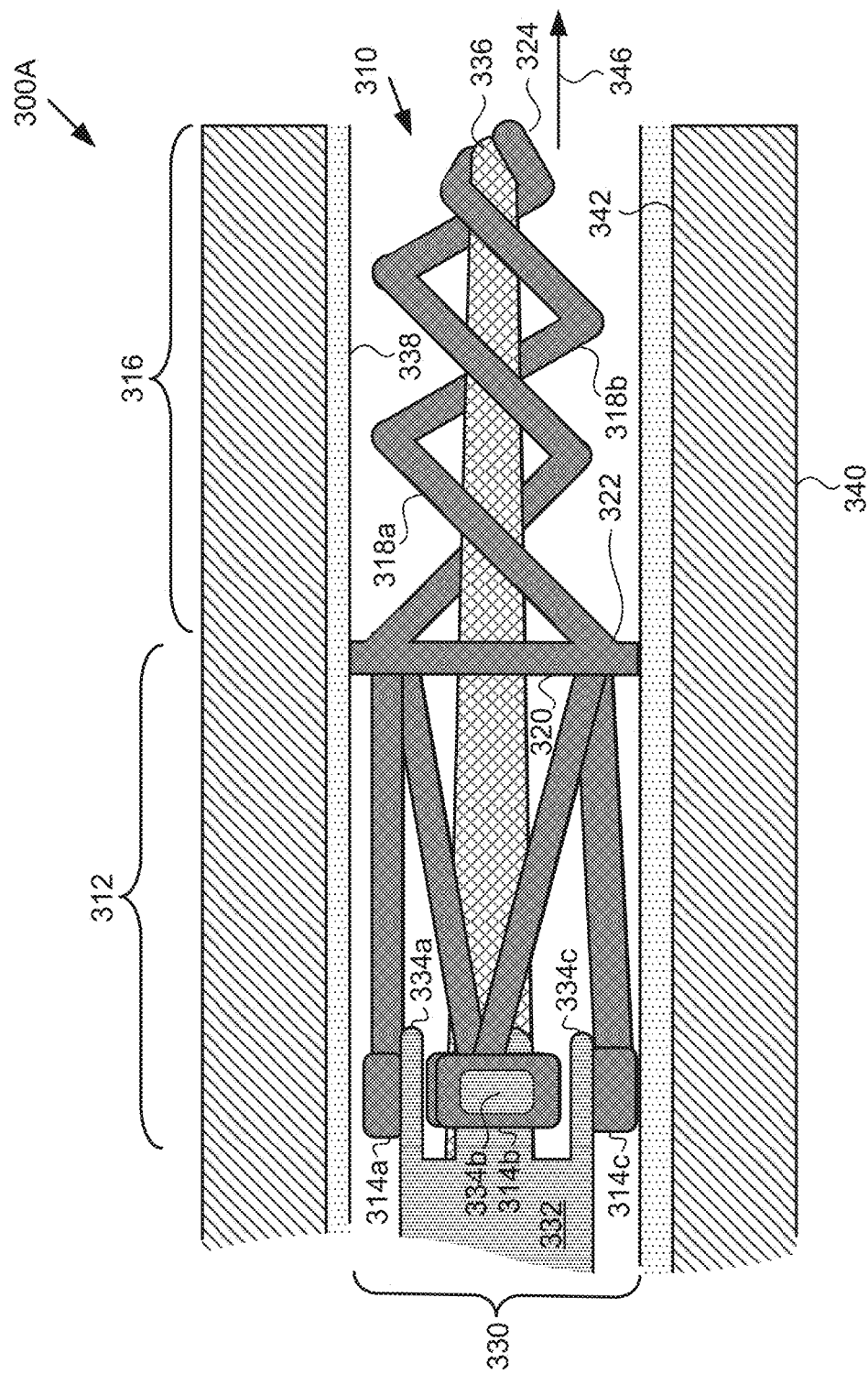
FIG. 3A shows a cross-sectional side view of a portion of a coronary artery of a living subject in which an exemplary coronary artery check valve delivery tool has been inserted, corresponding to an initial action in the flowchart in FIG. 2.

Referring now to FIG. 3A, cross-sectional side view 300A in FIG. 3A shows a portion of coronary artery 340 of a living subject in which exemplary coronary artery check valve delivery tool 330 has been inserted, after completion of action 201 of flowchart 200. As shown in FIG. 3A, coronary artery check valve delivery tool 330 includes delivery sheath 338, activation wire 336, and implantation catheter 332 having tabs 334a, 334b, and 334c. In addition, coronary artery check valve delivery tool 330 is shown to contain coronary artery check valve 310 including stent 312 having end 320 and anchors 314a, 314b, and 314c, as well as tapered helical coil 316 formed from interlaced wires 318a and 318b. Also shown in FIG. 3A are inner wall 342 of coronary artery 340, proximal end 322 of tapered helical coil 316, distal end 324 of tapered helical coil 316, and direction 346.

Figure 3B:
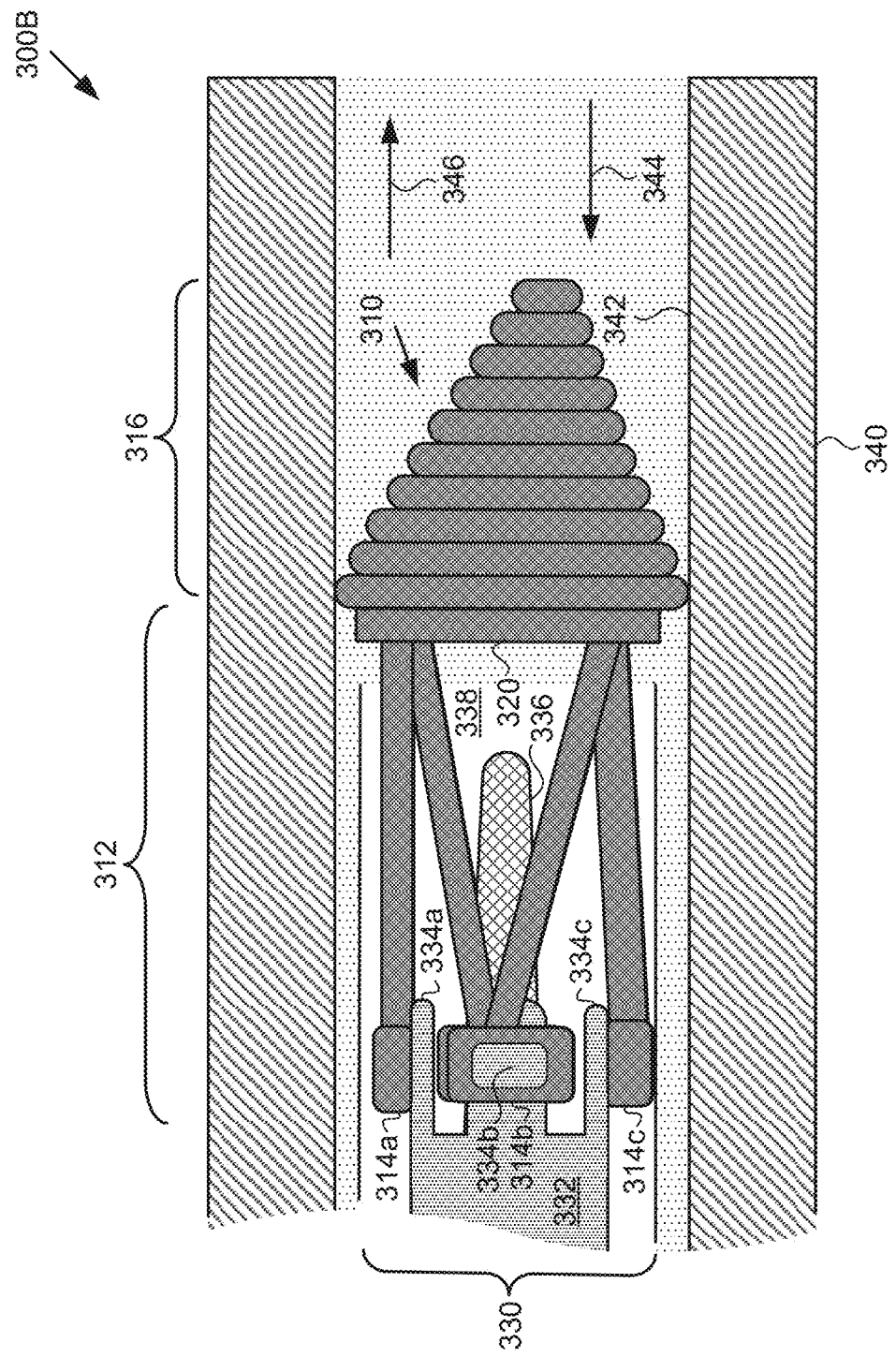
FIG. 3B shows a cross-sectional side view of a portion of a coronary artery of a living subject in which an exemplary coronary artery check valve is partially deployed and tested using a coronary artery check valve delivery tool, corresponding to an intermediate action in the flowchart in FIG. 2.
Figure 3C:
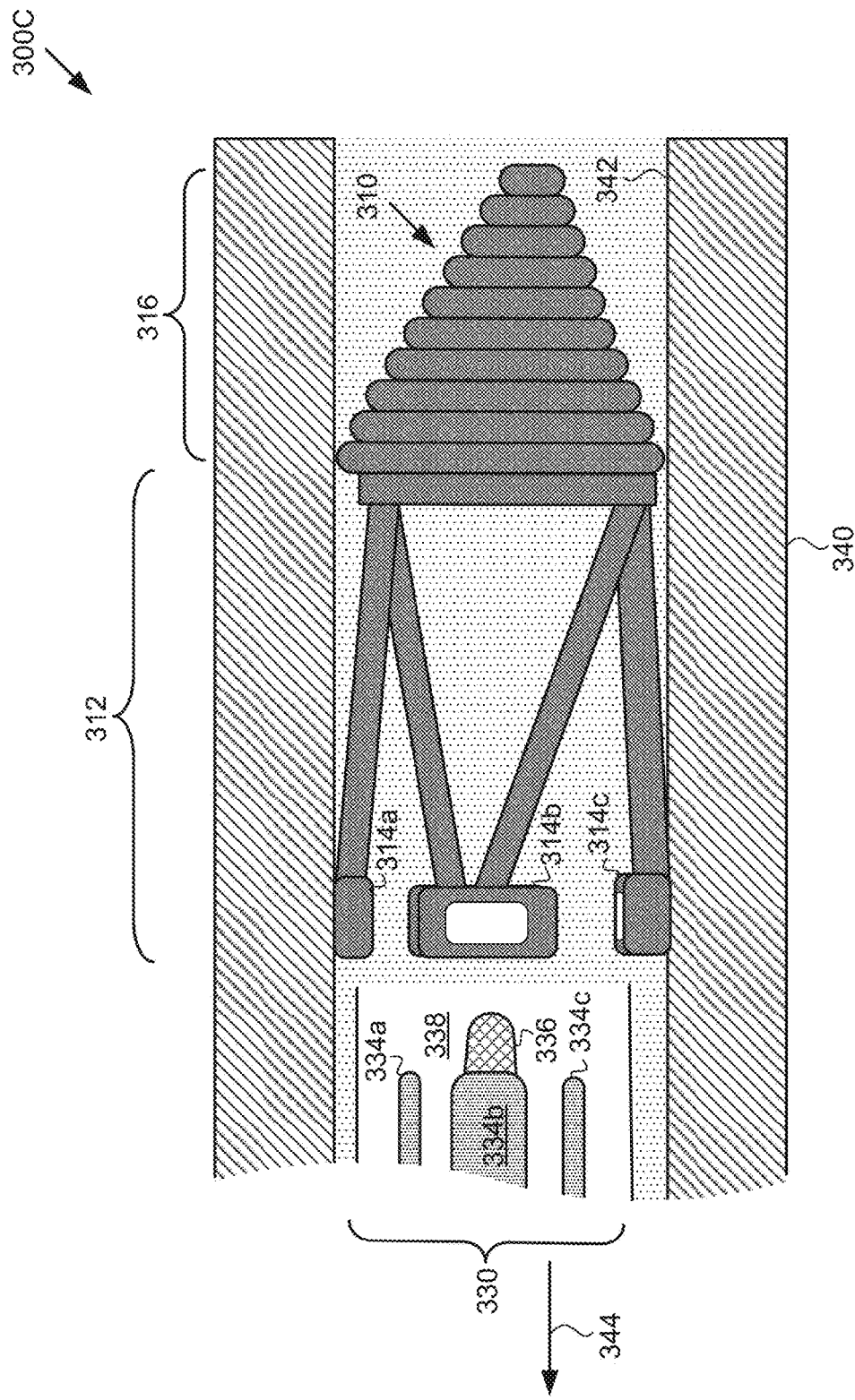
FIG. 3C shows a cross-sectional side view of a portion of a coronary artery of a living subject in which an exemplary coronary artery check valve is fully deployed after successful testing, corresponding to an intermediate action in the flowchart in FIG. 2.
Figure 3D:
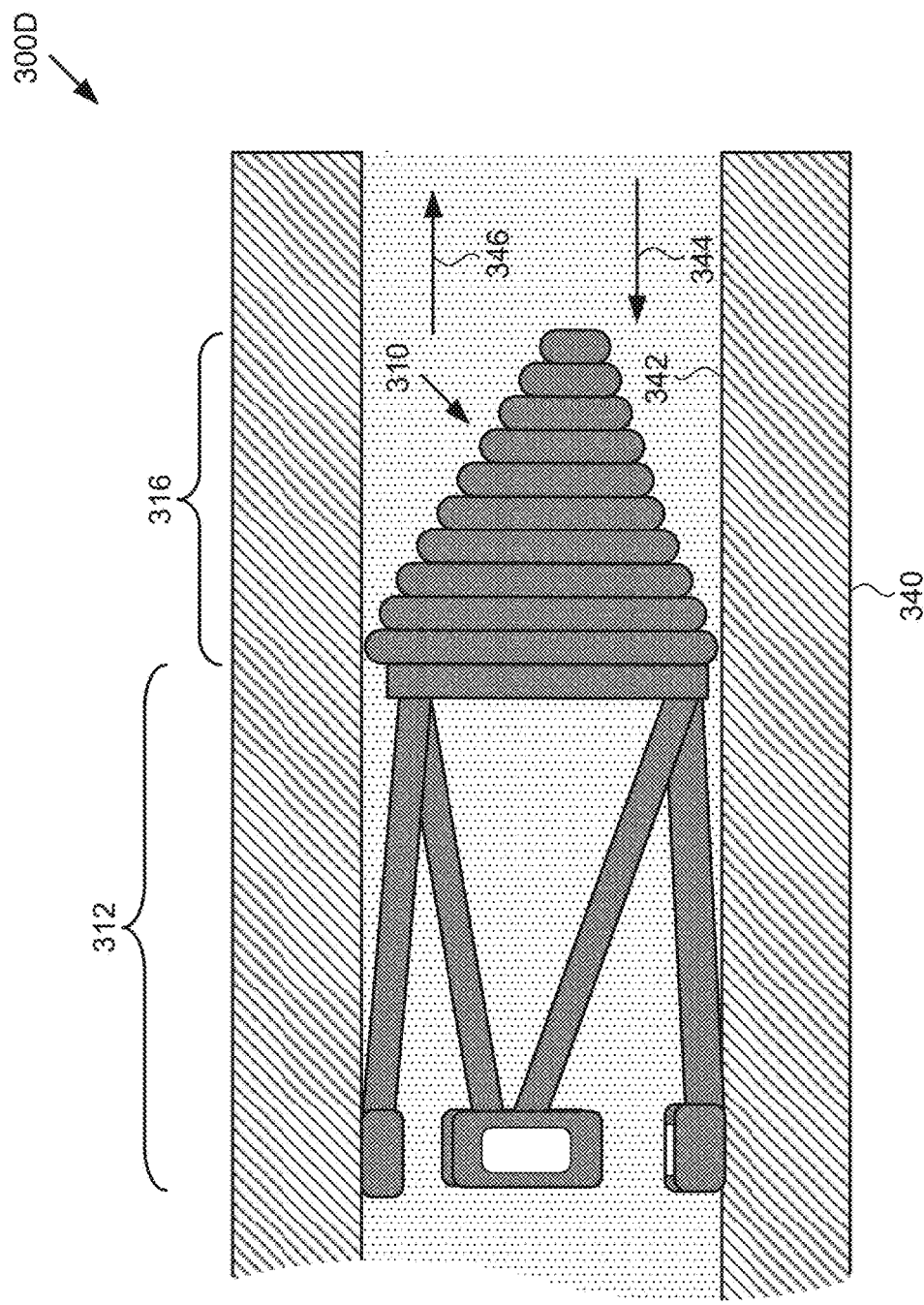
FIG. 3D shows a cross-sectional side view of a portion of a coronary artery of a living subject in which an exemplary coronary artery check valve is implanted, after withdrawal of a coronary artery check valve delivery tool from the living patient, corresponding to a final action in the flowchart in FIG. 2.

Coronary artery check valve 310 in FIG. 3A, as well as in FIGS. 3B, 3C, and 3D, corresponds in general to coronary artery check valve 110A/110B in FIGS. 1A and 1B. Thus, stent 312 having end 320 and anchors 314a, 314b, and 314c corresponds in general to stent 112 having end 120 and anchors 114a, 114b, and 114c, and those corresponding features can share any of the characteristics attributed to either corresponding feature by the present disclosure.

In addition, tapered helical coil 316 including wires 318a/318b corresponds in general to tapered helical coil 116 including wires 118/118a/118b, and those corresponding features can share any of the characteristics attributed to either corresponding feature by the present disclosure. That is to say, interlaced wires 318a and 318b may be formed of nitinol. Moreover, direction 346, in FIG. 3A, as well as in FIGS. 3B and 3D, corresponds to direction 146 in FIG. 1A.

Continuing to refer to FIG. 3A with further reference to flowchart 200, in FIG. 2, flowchart 200 begins with inserting coronary artery check valve delivery tool 330 into coronary artery 340 of a living subject (action 201). Delivery sheath 338, implantation catheter 332, and activation wire 336 of coronary artery check valve delivery tool 330 may be implemented as flexible elements suitable for insertion into coronary artery 340 of the living subject.

According to the implementation shown by FIG. 3A, when coronary artery check valve 110A/110B/310 is contained within delivery sheath 338 of coronary artery check valve delivery tool 330, anchors 114a/314a, 114b/314b, and 114c/314c of coronary artery check valve 110A/110B/310 are secured by respective tabs 334a, 334b, and 334c of implant catheter 332. As further shown by FIG. 3A, when coronary artery check valve 110A/110B/310 is contained within delivery sheath 338 of coronary artery check valve delivery tool 330, tapered helical coil 116/316 is expanded longitudinally in direction 146/346 by activation wire 336, corresponding to an open state of coronary artery check valve 110A/110B/310. That is to say, distal end 124/324 of tapered helical coil 116/316 is extended away from proximal end 122/322 of tapered helical coil 116/316 in direction 146/346 by activation wire 336 when coronary artery check valve 110A/110B/310 is contained within coronary artery check valve delivery tool 330.

Referring to cross-sectional side view 300B in FIG. 3B, flowchart 200 continues with partially deploying, in coronary artery 340 of the living subject, coronary artery check valve 110A/110B/310 having tapered helical coil 116/316 coupled to stent 112/312 (action 202). It is noted that direction 344 shown in FIG. 3B, as well as in FIGS. 3C and 3D, corresponds to direction 144 in FIG. 1A.

Partial deployment of coronary artery check valve 110A/110B/310 may be performed using coronary artery check valve delivery tool 330, by retracting activation wire 336 and delivery sheath 338 from tapered helical coil 116/316. For example, and as shown in FIG. 3B, activation wire 336 may be retracted in direction 144/344 past end 120/320 of stent 112/312. In addition, and as further shown in FIG. 3B, delivery sheath 338 may be retracted in direction 144/344 to a position between end 120/320 of stent 112/312 and anchors 114a/314a, 114b/314b, and 114c/314c of stent 112/312.

Continuing to refer to cross-sectional side view 300B in FIG. 3B, flowchart 200 continues with testing the functionality of coronary artery check valve 110A/110B/310 in the living subject (action 203). Proper functionality of coronary artery check valve 110A/110B/310 in the absence of the extension force provided by activation wire 336 in FIG. 3A includes longitudinal compression of tapered helical coil 116/316 in direction 144/344. That longitudinal compression of tapered helical coil 116/316 serves to close coronary artery check valve 110A/110B/310 in order to prevent retrograde blood flow in direction 144/344.

Referring to cross-sectional side view 300C in FIG. 3C, flowchart 200 continues with fully deploying coronary artery check valve 110A/110B/310 using coronary artery check valve delivery tool 330, if coronary artery check valve 110A/110B/310 functions properly during testing (action 204). Full deployment of coronary artery check valve 110A/110B/310 may be performed using coronary artery check valve delivery tool 330, by releasing anchors 114a/314a, 114b/314b, and 114c/314c from respective tabs 334a, 334b, and 334c of implantation catheter 332, and retracting implantation catheter 332, activation wire 336, and delivery sheath 338 from stent 112/312.

For example, after release of anchors 114a/314a, 114b/314b, and 114c/314c of stent 112/312 from respective tabs 334a, 334b, and 334c, implantation catheter 332, activation wire 336, and delivery sheath 338 may be retracted in direction 144/344 past anchors 114a/314a, 114b/314b, and 114c/314c. As a result, anchors 114a/314a, 114b/314b, and 114c/314c are freed to secure stent 112/312 to inner wall 342 of coronary artery 340, while tapered helical coil 116/316 regulates blood in coronary artery 340.

Referring to cross-sectional side view 300D in FIG. 3D, flowchart 200 can conclude with withdrawing coronary artery check valve delivery tool 330 from the living subject, leaving coronary artery check valve 110A/110B/310 implanted in the living subject (action 205). As shown in FIG. 3D, withdrawal of coronary artery check valve delivery tool 330 from the living subject leaves coronary artery check valve 110A/110B/310 implanted in coronary artery 340. In one implementation of the present application, as understood by one of ordinary skill in the art, testing to determine whether the coronary artery check valve functions properly in the living subject (action 203) may be skipped, and actions 202 and 204 may be merged, such that the coronary artery check valve is deployed in the coronary artery of the living subject using coronary artery check valve delivery tool.

As a result, coronary artery check valve 110A/110B/310 can function to prevent retrograde flow of the coronary blood supply of the living subject during diastole of the heart of the living subject. As a specific example, coronary artery check valve 110A/110B/310 can prevent retrograde flow of the coronary blood supply during diastole by closing during systole of the heart when tapered helical coil 116/316 compresses longitudinally in direction 144/344, and opening when tapered helical coil 116/316 expands longitudinally in direction 146/346 to permit blood flow into the coronary artery when a coronary pressure of the living subject drops below diastolic blood pressure.

Figure 4:
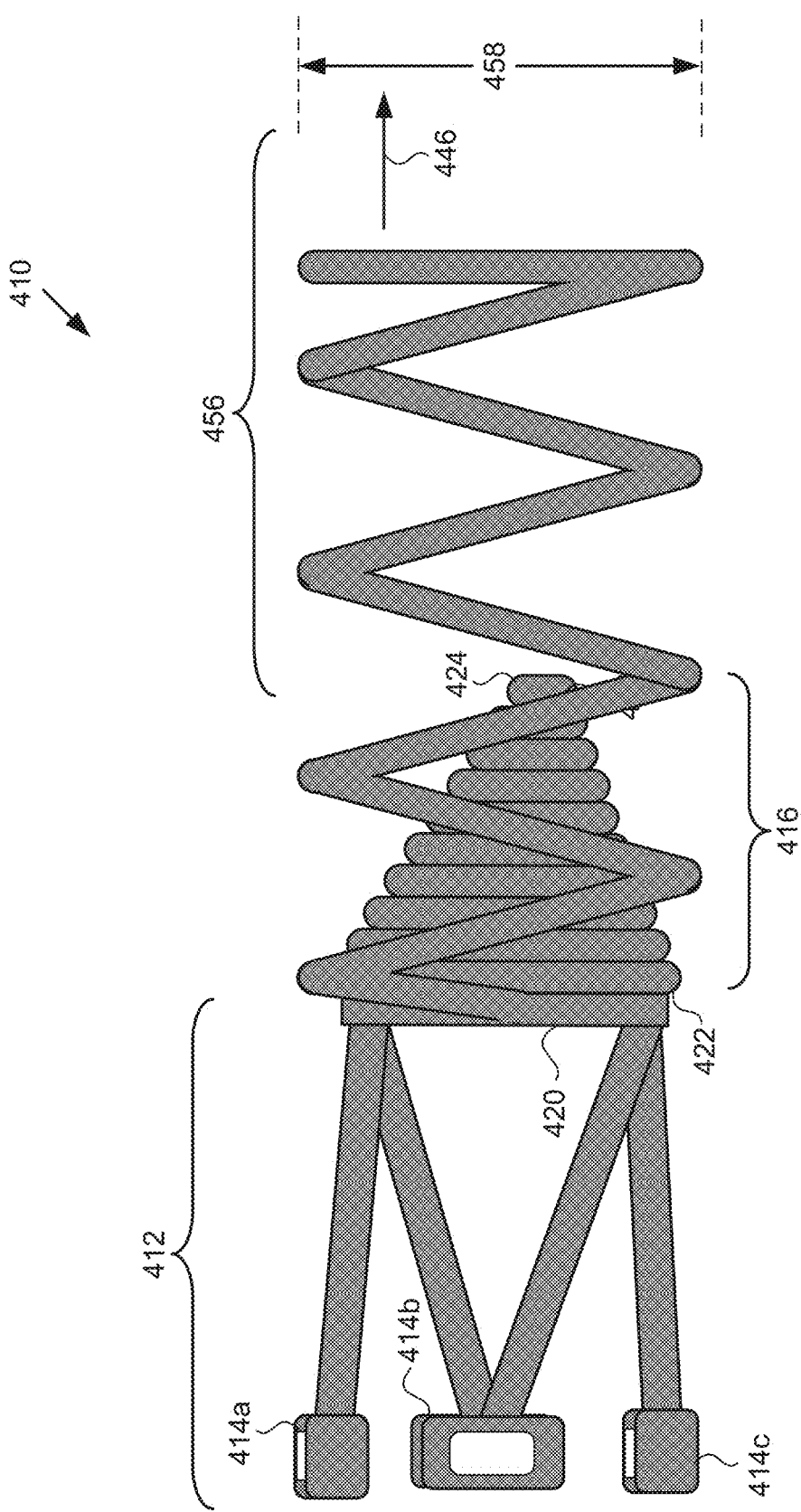
FIG. 4 shows a side view of a coronary artery check valve in a closed state, according to another exemplary implementation.

FIG. 4 shows a side view of coronary artery check valve 410 in a closed state, according to another exemplary implementation. As shown in FIG. 4, coronary artery check valve 410 includes stent 412 and tapered helical coil 416 having proximal end 422 coupled to end 420 of stent 412. Also shown in FIG. 4 are anchors 414a, 414b, and 414c of stent 412, distal end 424 of tapered helical coil 416, guide coil 456 having diameter 458, and direction 446.

Stent 412 having end 420 and anchors 414a, 414b, and 414c corresponds in general to stent 112/312 having end 120/320 and anchors 114a/314a, 114b/314b, and 114c/314c in FIGS. 1A and 3A through 3D, and may share any of the characteristics attributed to those corresponding features in the present disclosure. In addition, tapered helical coil 416 having proximal end 422 and distal end 424 corresponds in general to tapered helical coil 116/316 having proximal end 122/322 and distal end 124/324 in FIGS. 1A, 1B, and 3A through 3D, and may share any of the characteristics attributed to those corresponding features in the present disclosure. That is to say, tapered helical coil 416 may be formed by a single wire, or two or more interlaced wires, which may be a nitinol wire or wires, for example. Moreover, it is noted that direction 446 corresponds to direction 146/346 in FIGS. 1A, 3A, 3B, and 3D.

According to the exemplary implementation shown in FIG. 4, guide coil 456 is coupled to end 120/320/420 of stent 112/312/412 and may include multiple windings having substantially constant diameter 458. As shown in FIG. 4, guide coil 456 may surround tapered helical coil 116/316/416, and may extend beyond distal end 124/324/424 of tapered helical coil 116/316/416 in direction 146/346/446. In one implementation, guide coil 456 may be included as part of coronary artery check valve 110A/110B/310/410 to ensure proper alignment of tapered helical coil 116/316/416 in coronary artery 340 of the living subject. In addition, guide coil 456 provides protection for tapered helical coil 116/316/416 during and after implantation of coronary artery check valve 110A/110B/310/410 in the living patient. In implementations in which stenosis is a concern for the living subject, diameter 458 of guide coil 456 can be sized larger than the inner diameter of coronary artery 340 in which coronary artery check valve 110A/110B/310/410 is implanted.

Figure 5:
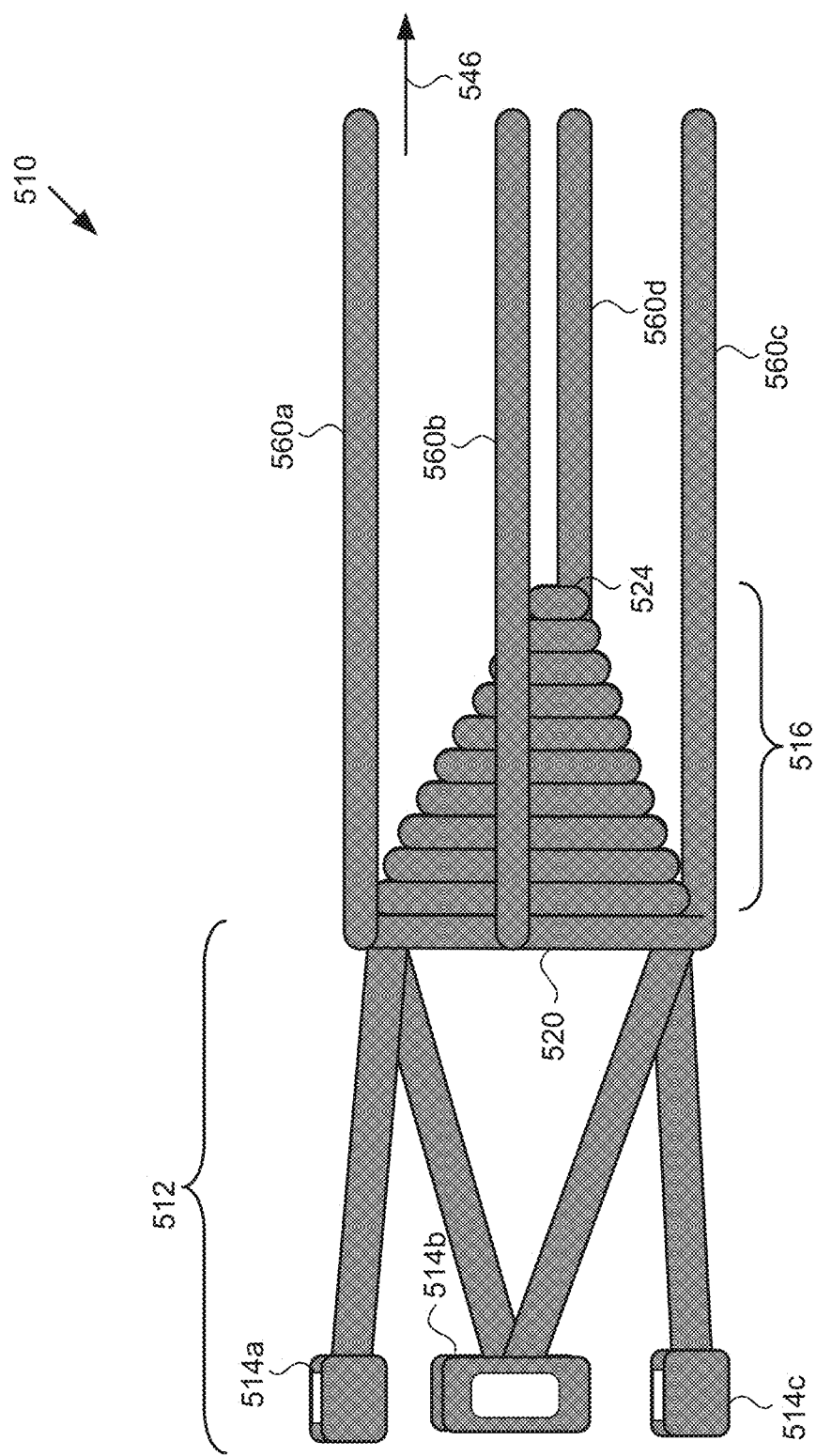
FIG. 5 shows a side view of a coronary artery check valve in a closed state, according to yet another exemplary implementation.

FIG. 5 shows a side view of coronary artery check valve 510 in a closed state, according to yet another exemplary implementation. As shown in FIG. 5, coronary artery check valve 510 includes stent 512 and tapered helical coil 516 having a proximal end coupled to end 520 of stent 512. Also shown in FIG. 5 are anchors 514a, 514b, and 514c of stent 512, distal end 524 of tapered helical coil 516, guide wires 560a, 560b, 560c, and 560d (hereinafter "guide wires 560a-560d"), and direction 546.

Stent 512 having end 520 and anchors 514a, 514b, and 514c corresponds in general to stent 112/312/412 having end 120/320/420 and anchors 114a/314a/414a, 114b/314b/414b, and 114c/314c/414c in FIGS. 1A, 3A through 3D, and 4, and may share any of the characteristics attributed to those corresponding features in the present disclosure. In addition, tapered helical coil 516 having distal end 524 corresponds in general to tapered helical coil 116/316/416 having distal end 124/324/424 in FIGS. 1A, 1B, 3A through 3D, and 4, and may share any of the characteristics attributed to those corresponding features in the present disclosure. That is to say, tapered helical coil 516 may be formed by a single wire, or two or more interlaced wires, which may be a nitinol wire or wires, for example. Moreover, it is noted that direction 546 corresponds to direction 146/346/446 in FIGS. 1A, 3A, 3B, 3D, and 4.

According to the exemplary implementation shown in FIG. 5, guide wires 560a-560d are coupled to end 120/320/420/520 of stent 112/312/412/512. It is noted that although the exemplary implementation shown in FIG. 5 depicts guide wires 560a-560d as including four wires, in other implementations, guide wires 560a-560d may include fewer, or more, than four wires. Moreover, like wires 118/118a/118/318a/318b of tapered helical coil 116/316/416/516, guide wires 560a-560d may take the form of nitinol wires.

As shown in FIG. 5, guide wires 560a-560d may extend beyond distal end 124/324/424/524 of tapered helical coil 116/316/416/516 in direction 146/346/446/546. In one implementation, guide wires 560a-560d may be included as part of coronary artery check valve 110A/110B/310/410/510 to ensure proper alignment of tapered helical coil 116/316/416/516 in coronary artery 340 of the living subject. In addition, guide wires 560a-560d provide protection for tapered helical coil 116/316/416/516 during and after implantation of coronary artery check valve 110A/110B/310/410/510 in the living patient.

Figure 6:
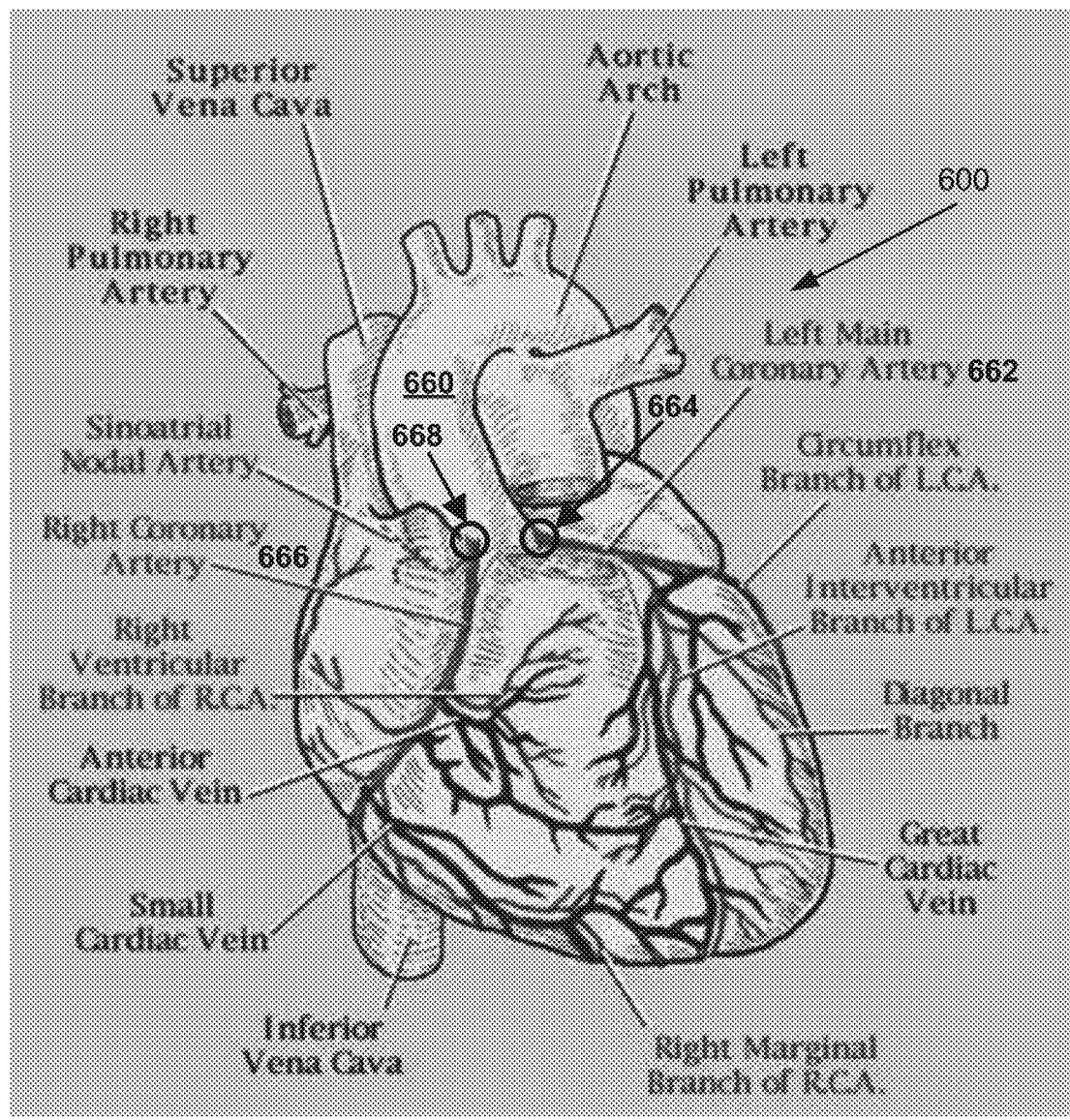
FIG. 6 is a diagram of the anatomy of the human heart, showing locations suitable for implantation of a coronary artery check valve.

FIG. 6 is a diagram of the anatomy of human heart 600, identifying locations suitable for implantation of a coronary artery check valve, according to various implementations of the present inventive principles. Among the several features of human heart 600 referenced in FIG. 6, attention is directed to aorta 660, left main coronary artery 662, and coronary ostia 664 of left main coronary artery 662, where left main coronary artery 662 enters the root of aorta 660. Attention is also directed to right coronary artery 666 and coronary ostia 668 of right coronary artery 666, where right coronary artery 666 enters the root of aorta 660.

Coronary artery check valve 110A/110B/310/410/510 is configured to be implanted at any point along left main coronary artery 662, including coronary ostia 664, as well as at any point along right coronary artery 666, including coronary ostia 668. When implanted, coronary artery check valve 110A/110B/310/410/510 is configured to advantageously prevent retrograde flow of the coronary blood supply during diastole of human heart 600.

Thus, the present application discloses a coronary artery check valve and method for its implantation. As discussed above, the coronary artery check valve disclosed herein may be implanted in one or both of the coronary ostia, or at any point along the coronary arteries, to prevent retrograde flow of the coronary blood supply during diastole. The coronary artery check valve is configured to allow the coronary artery in which it is implanted to reach systolic blood pressure during systole, and to remain at systolic blood pressure until the coronary pressure drops below diastolic blood pressure. When the coronary pressure drops below diastolic blood pressure, the coronary artery check valve is further configured to open so as to advantageously allow additional blood flow into the coronary artery. Consequently, the coronary artery check valve disclosed in the present application is suitable for use in combination with beta blockers, thereby enabling the desirable increase in LVEF associated with use of those drugs, while advantageously avoiding reduction in coronary blood flow due to low diastolic blood pressure.

From the above description it is manifest that various techniques can be used for implementing the concepts described in the present disclosure without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present disclosure is not limited to the particular implementations described herein, but many rearrangements, modifications, and substitutions are possible without departing from the scope of the present disclosure.

What is claimed is:

1. A method of implanting a coronary artery check valve in a living subject, the coronary artery check valve having a tapered helical coil coupled to a stent, the method comprising:
    inserting a coronary artery check valve delivery tool into a coronary artery of the living subject;
    deploying, using coronary artery check valve delivery tool, the coronary artery check valve in the coronary artery of the living subject;
    withdrawing the coronary artery check valve delivery tool from the living subject; and
    leaving, after the withdrawing the coronary artery check valve delivery tool, the coronary artery check valve implanted in the living subject to prevent retrograde flow of a coronary blood supply during diastole of a heart of the living subject;
    wherein the coronary artery check valve further comprises a guide coil coupled to an end of the stent, the guide coil having a substantially constant diameter.

2. A method of implanting a coronary artery check valve in a living subject, the coronary artery check valve having a tapered helical coil coupled to a stent, the method comprising:
    inserting a coronary artery check valve delivery tool into a coronary artery of the living subject;
    deploying, using coronary artery check valve delivery tool, the coronary artery check valve in the coronary artery of the living subject;
    withdrawing the coronary artery check valve delivery tool from the living subject; and leaving, after the withdrawing the coronary artery check valve delivery tool, the coronary artery check valve implanted in the living subject to prevent retrograde flow of a coronary blood supply during diastole of a heart of the living subject;

wherein the coronary artery check valve further comprises a plurality of guide wires coupled to an end of the stent and extending beyond a distal end of the tapered helical coil.

3. A method of implanting a coronary artery check valve in a living subject, the coronary artery check valve having a tapered helical coil coupled to a stent, the method comprising:

inserting a coronary artery check valve delivery tool into a coronary artery of the living subject;

deploying, using coronary artery check valve delivery tool, the coronary artery check valve in the coronary artery of the living subject;

withdrawing the coronary artery check valve delivery tool from the living subject; and leaving, after the withdrawing the coronary artery check valve delivery tool, the coronary artery check valve implanted in the living subject to prevent retrograde flow of a coronary blood supply during diastole of a heart of the living subject;

wherein the tapered helical coil is surrounded by the stent.

\* \* \* \* \*